United States Patent [19]

Calvin

[11] Patent Number: 5,098,843
[45] Date of Patent: Mar. 24, 1992

[54] APPARATUS FOR THE HIGH EFFICIENCY TRANSFORMATION OF LIVING CELLS

[76] Inventor: Noel M. Calvin, 4201 Page Mill Rd., Los Altos, Calif. 94022

[21] Appl. No.: 549,957

[22] Filed: Jul. 9, 1990

Related U.S. Application Data

[63] Continuation of Ser. No. 57,980, Jun. 4, 1987, abandoned.

[51] Int. Cl.[5] .................... C12N 13/00; C12N 15/00
[52] U.S. Cl. ...................... 435/287; 435/173; 435/172.1; 935/52; 935/85
[58] Field of Search .............. 435/173, 172.2, 172.1, 435/172.3, 287, 289; 935/52, 53, 93, 89, 85; 204/299 R, 183.1, 180.1

[56] References Cited

U.S. PATENT DOCUMENTS

| | | | |
|---|---|---|---|
| 4,561,961 | 12/1985 | Hofmann | 204/299 R |
| 4,699,881 | 10/1987 | Matschke | 435/287 X |
| 4,750,100 | 6/1988 | Ragsdale | 363/86 |

Primary Examiner—John Niebling
Assistant Examiner—John S. Starsiak, Jr.
Attorney, Agent, or Firm—Philip D. Junkins

[57] ABSTRACT

Apparatus and methodology for the transformation of living cells by the introduction of DNA thereto through transient pores created in the cell walls by the highly efficient electroporation of such cells in a liquid suspension with DNA. High efficiency electroporation is accomplished by the generation of a high voltage electrical pulse with precise characteristics determined necessary to optimize cell transformation and the application of such pulse to a sample of such suspension or by continuous flow of the suspension through a static electrical field under flow conditions to simulate the precise characteristics of such high voltage pulse. Thus, the suspension, whether treated as a non-flowing sample or as a continuous flow liquid suspension of cells in admixture with DNA, is subjected to a high intensity electric field at its maximum intensity in no more than about 100 microseconds and thereafter to reduced field intensity to zero field intensity in no more than about 5,000 microseconds. The high intensity pulse, or static electrical field with suspension flow therethrough simulating the characteristics of such pulse, porates the wall of the cells in suspension thereby allowing the introduction of DNA into the cells with a high survival rate for such cells.

6 Claims, 3 Drawing Sheets ns5,098,843

APPARATUS FOR THE HIGH EFFICIENCY TRANSFORMATION OF LIVING CELLS

This is a continuation of my co-pending application Ser. No. 07/057,980 filed June 4, 1987 now abandoned.

BACKGROUND OF THE INVENTION

It is known that transient high intensity electric fields can cause reversible, and at higher intensities, irreversible pores to form in lipid by-layers such as those that form membranes surrounding eukaryotic and prokaryotic cells. This principle forms the basis for a technique called "electroporation" which is of great and increasing importance to the emerging bio-technology industry. Of central importance to this industry is the process of "transformation" of cells in culture, a process whereby a cell is induced to express a gene whose product causes the cell to be commercially useful in some way. Currently, this usually means that the cell will produce a protein (e.g., insulin), which it does not normally produce, in large quantities. The protein is then harvested and purified for commercial purposes.

The process of transformation, reduced to its most basic level, requires two steps: 1) a sample of DNA containing the necessary sequences for the production of the desired product must be created, and 2) the DNA must be introduced into the living cells that are to be transformed. The second step involves a delicate compromise-the cell membrane must be weakened sufficiently to allow the DNA to diffuse into the cell, while not being weakened so much that the essential components of the cell leak out, thereby killing the cell.

Many methods have been employed to weaken cell membranes for the purpose of cell transformation, including physical shocks such as freezing, thawing, exposure to high temperatures or osmotic shock, chemical treatments such as detergents and calcium salts, and enzymatic treatments with proteolytic enzymes or lysozymes. These techniques all suffer from a common disadvantage-the damage they do to the cell membrane lasts until the cell actively repairs it, which many cells may never be able to accomplish. The result of this is that treatments sufficient to allow large amounts of DNA into the cells kill virtually all of the cells, while treatments mild enough to allow a large percentage of the cells to survive allow too little DNA to enter the cells.

The technique of electroporation overcomes this problem, because it generates holes or "pores" in the cellular membrane that last only a few milliseconds. This is because the pores are self-healing. Because of this, an electroporation resulting in a given cell survival allows much more DNA to enter the cells than any of the other techniques, thus achieving much higher transformation frequencies. In addition, electroporation has been shown to work in organisms highly resistant to transformation with any other method.

Electroporation has been used successfully on several eukaryotic cell types, including both animal and plant cell types. However, attempts to apply the technique to smaller cells, such as bacteria, have yielded uselessly low transformation rates. Since most commercial applications of recombinant DNA technology require that a gene be expressed in bacteria suitable of mass production, the development of a technique allowing the electroporation of bacterial cells is of great importance to the industry.

It is an object of the present invention to provide apparatus for the highly efficient transformation of living cells by the introduction of DNA thereto through transient pores created in the cell walls by electroporation.

It is a further object of the invention to provide apparatus for electroporating living cells with cell transformation efficiencies in excess of $10^9$ bacterial transformants per microgram of DNA.

Another object of the invention is to provide apparatus for the high efficiency transformation, by electroporation, of living bacterial, plant and animal cells in a suspension including DNA.

Yet another object of the invention is to provide a method for the transformation of living cells by the introduction of DNA thereto through transient pores created in the cell walls by the highly efficient electroporation of such cells in suspension with DNA.

Other objects and advantages of the invention will be apparent from the following detailed description of apparatus and methodology for accomplishing the highly efficient transformation of living cells by electroporation in accordance with the invention taken together the accompanying drawing figures.

SUMMARY OF THE INVENTION

The present invention relates to apparatus and methodology for the transformation of living cells by the introduction of DNA thereto through transient pores created in the cell walls by the highly efficient electroporation of such cells in suspension with DNA. High efficiency electroporation is accomplished by the generation of a high voltage pulse or wave with precise characteristics determined necessary to optimize cell transformation and the application of such pulse or wave to a suspension of cells and DNA. Thus, in accordance with the invention, a pulse generator develops a transient high intensity electric pulse having a pulse rise time to its maximum intensity of no more than about 100 microseconds, a pulse fall time of no more than about 5,000 microseconds, and a pulse width (pulse rise, dwell and pulse fall time) of no more than about 5,000 microseconds. The developed high intensity pulse or wave has a field strength of up to about 15,000 volts per centimeter and is applied in a cell transformation zone to a suspension of living cells in admixture with DNA. The high intensity electric pulse or wave porates the walls of the cells in the suspension thereby allowing the introduction of DNA with a high survival rate for such cells.

The cell transformation zone includes two metallic electrodes for applying the high intensity electric pulse or wave to the suspension of cells and DNA. These electrodes are positioned so that the cell/DNA suspension is suspended between such electrodes by surface tension. The electrodes are designed for accepting very small batch or sample quantities of cell suspensions or alternatively for accepting a continuous flow of cell suspensions. Where continuous flow methodology is practiced, the desired effects of a transient high intensity electric pulse are simulated by varying and controlling the flow rates of the cell suspension as such suspension travels through an electroporation chamber having a venturi shaped passageway including appropriately shaped electrodes impressed with a high level of DC voltage.

BRIEF DESCRIPTION OF THE DRAWING FIGURES

In the accompanying drawing sheets:

Figure 5:
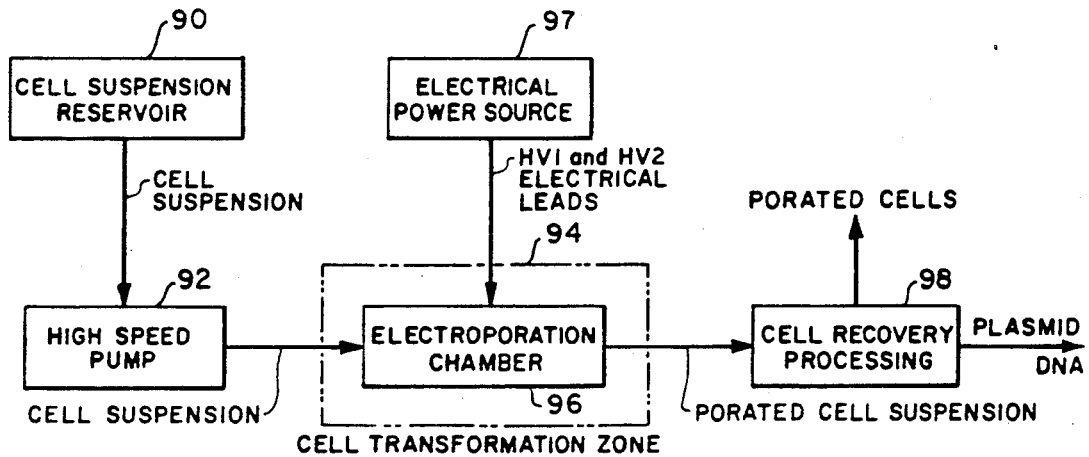
Figure 6:
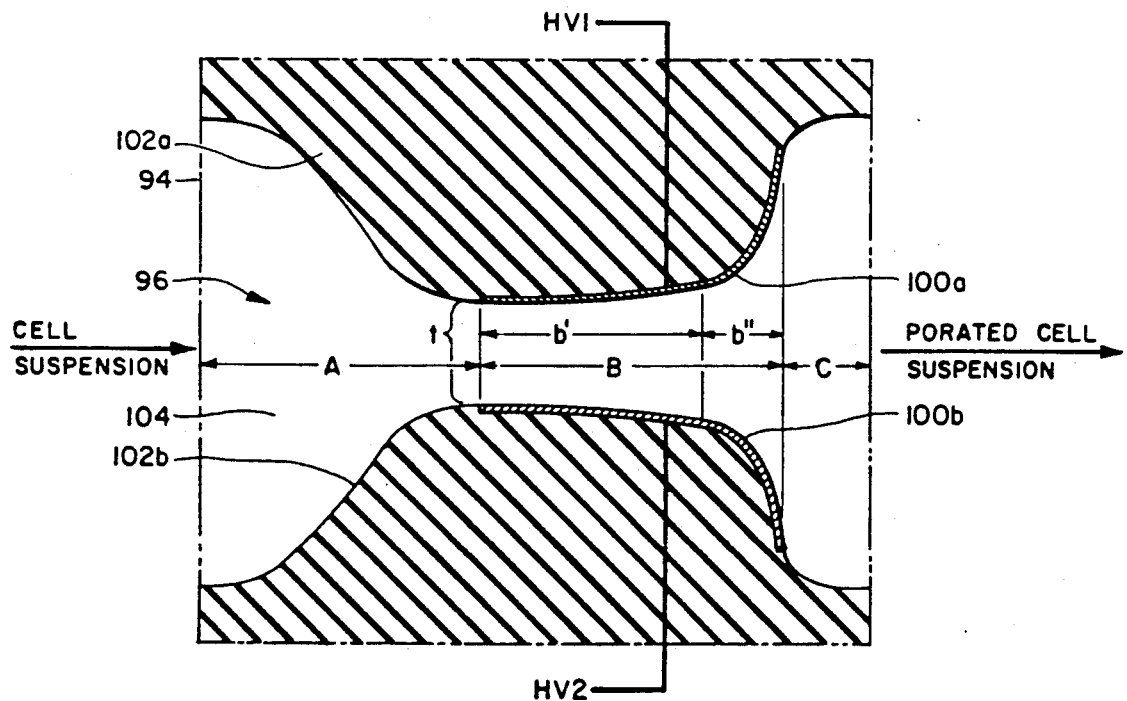

FIG. 5 is a block diagram of apparatus for the continuous flow transformation of living cells in suspension with DNA by electroporation in accordance with the invention; and FIG. 6 is a schematic side cross-sectional view of a continuous flow electroporation chamber within a cell transformation zone showing electrode configurations duplicating the effect of a transient high intensity electric field.

DETAILED DESCRIPTION OF THE PREFERRED EMBODIMENTS

As previously indicated, the purpose or objective of the present invention is to generate (or structurally simulate) a high voltage pulse with the precise characteristics necessary to optimize the transformation by electroporation of living cells in a suspension of DNA.

The required pulse characteristics are as follows: 1) a pulse or wave rise time of between approximately 10 to 100 microseconds, 2) a pulse or wave fall time of approximately 1–5 milliseconds (1000 to 5000 microseconds), and a pulse or wave width (pulse rise, dwell and pulse fall time) of approximately 1–5 milliseconds (1000 to 5000 microseconds). The maximum field strength in the transformation zone must be at least 12–15 kvolts/cm. In a first described preferred embodiment of the invention, a high intensity electric pulse of appropriate wave configuration and time span is applied by electrodes to small batch or sample quantities of suspended living cells with DNA in a cell transformation zone under non-flow conditions.

Circuit Description

Figure 1:
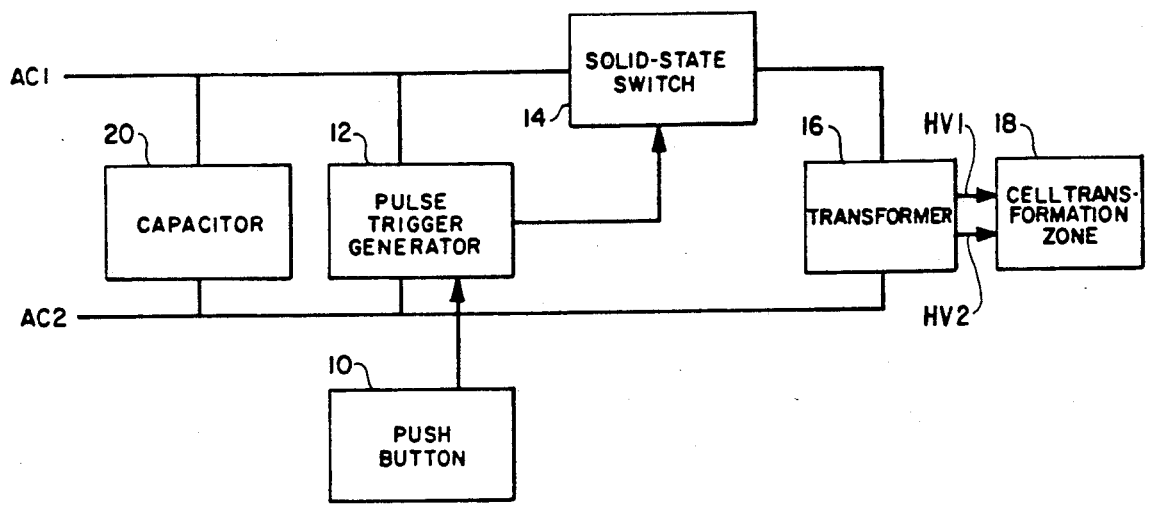
FIG. 1 is a block diagram of apparatus for the transformation of living cells by electroporation of DNA into such cells in accordance with the present invention.

A block diagram of the first preferred embodiment is shown in FIG. 1. A standard 110 volt 50–60 Hz, 10 amp powerline AC1/AC2 is used as the power supply. When the button 10 is pressed, the control circuit 12 generates a trigger pulse that is timed to occur at a specific point in the cycle of the power supply voltage, e.g., at a phase of 90 degrees. This trigger pulse causes the solid state switch 14 to turn on, thus applying voltage to the primary coil of transformer 16. The output of the transformer 16 is applied to the cell suspension sample in transformation zone 18. Capacitor 20 is optional, and can be used to decrease the rise time of the voltage pulse by providing the current necessary to charge the inherent capacitance of transformer 16. The capacitor 20 may be necessary if the transformer 16 is large, or if the powerline circuit has a high impedance.

Figure 2:
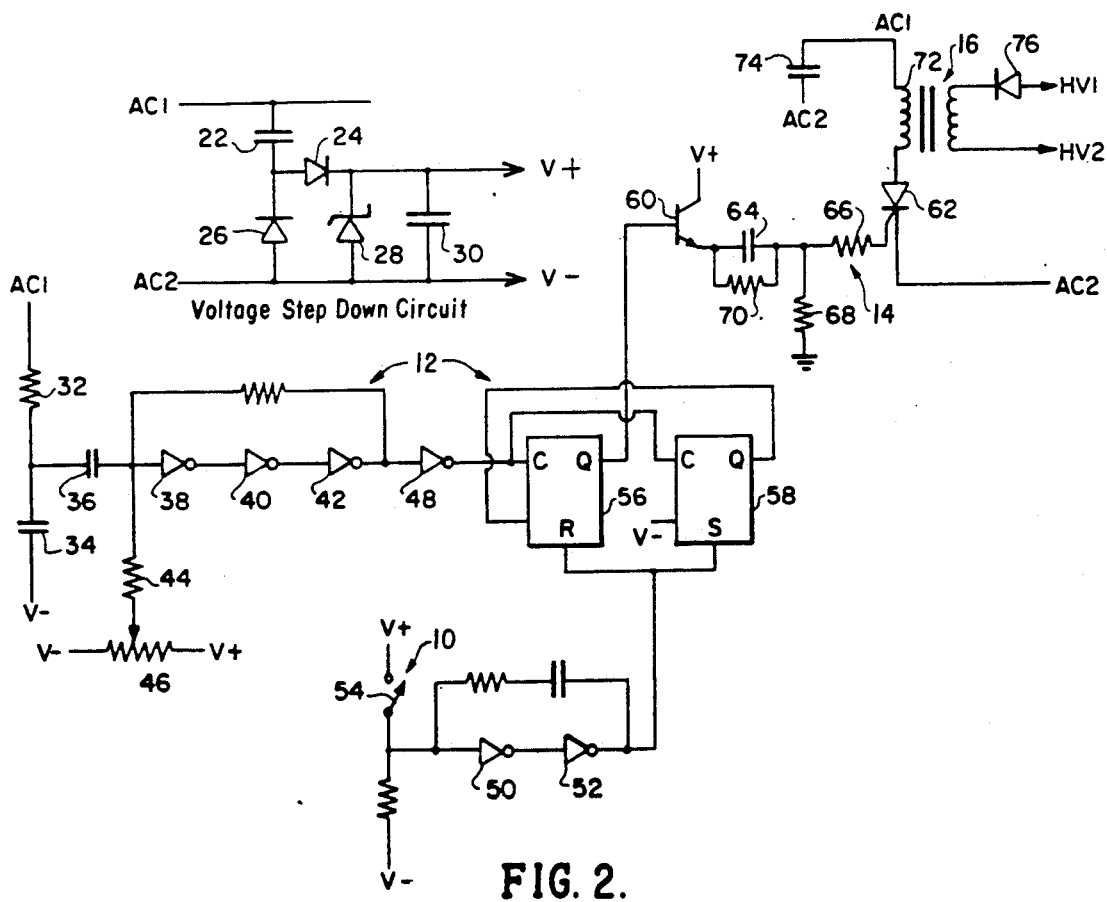
FIG. 2 is a schematic diagram of the electronic circuitry utilized in accordance with the invention to generate a transient high intensity electric field having pulse or wave characteristics necessary to effect the optimum transformation of living cells by electroporation of DNA into such cells.

A schematic circuit diagram of the first preferred embodiment is shown in FIG. 2. AC voltage (110–120 volts) is obtained from standard power lines and is fed into a voltage step down circuit via lead lines AC1 and AC2. Capacitor 22, rectifiers 24 and 26 and zener diode 28 form the voltage step down circuit with an output, via output leads V+ and V−, of approximately ten volts at one milliamp current. Capacitor 30, of such circuit, filters out power supply ripple. The output leads V+ and V− of the voltage step down circuit connect to the low voltage input leads V+ and V− at various points of the remaining circuitry shown in FIG. 2.

In the circuitry of FIG. 2, capacitor 34 and resistor 32 form a 90 degree phase shift network 12, generating a sine wave that is 90 degrees behind the line voltage. This voltage is fed through capacitor 36 into standard CMOS invertor gates 38, 40 and 42. These gates form a comparator whose threshold voltage is set by feedback resistor 44. Potentiometer 46 and resistor 44 allow fine adjustment of the threshold voltage. The output of gate 42 is connected to gate 48 which inverts the signal and decreases its rise and fall times. The output of gate 48 is approximately a square wave whose negative transition can be adjusted to occur plus or minus 40 degrees from the positive peak of the power line voltage.

CMOS invertors 50 and 52 form an ac-coupled Schmidt trigger circuit 10 to debounce the output of push button 54. The output of invertor 52 is fed into the reset input of CMOS D-type flip flop 56, and also into the set input of flip flop 58.

The circuitry of FIG. 2 operates as follows: When push button 54 is pressed, the output of invertor 52 goes high, causing the output of flip flop 58 to go high and preventing flip flop 56 from responding to the clock signal. When the button 54 is released, the output of invertor 52 goes low, enabling flip flop 56. On the next negative transition of the clock signal obtained from invertor 48, the output of flip flop 56 will go high.

The output of flip flop 56 is connected to transistor 60 of switch circuitry 14, which applies a high current trigger pulse to the gate of SCR 62. Capacitor 64 supplies the energy for the pulse, resistor 66 limits the gate current of the SCR, resistor 68 prevents false triggering of the SCR, and resistor 70 discharges the capacitor between pulses.

When the SCR 62 turns on, a voltage of approximately 170 volts is applied to the primary coil 72 of transformer 16. Capacitor 74 may be added to provide the current needed to charge the internal capacitance of the transformer quickly, thereby decreasing the rise time of the output voltage pulse. Diode 76 allows only the positive half of the output pulse to be fed into the sample chamber (cell transformation zone 18). On the next negative transition of the clock signal from invertor 48 the output of flip flop 56 goes low, causing the output of flip flop 58 to go low, locking flip flop 56 into the low state until the next time button 54 is pressed. The desired transient high voltage pulse, for application to the electrodes of the cell transformation zone, is derived from the foregoing circuitry via leads HV1 and HV2.

Figure 3:
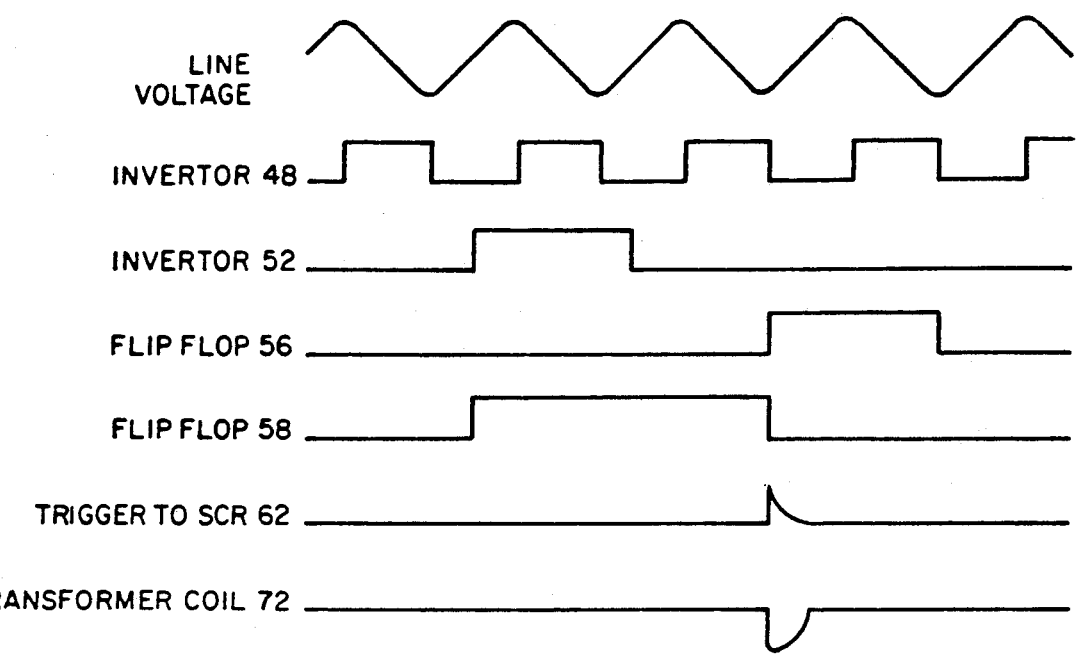
FIG. 3 illustrates the waveforms generated at various points in the circuitry of FIG. 2 by the circuitry components and subcircuits thereof.

The waveforms generated within the operation of the circuitry of FIG. 2 are shown in FIG. 3 and are identified by the circuit components with which they are associated.

Sample Transformation Zone

Figure 4:
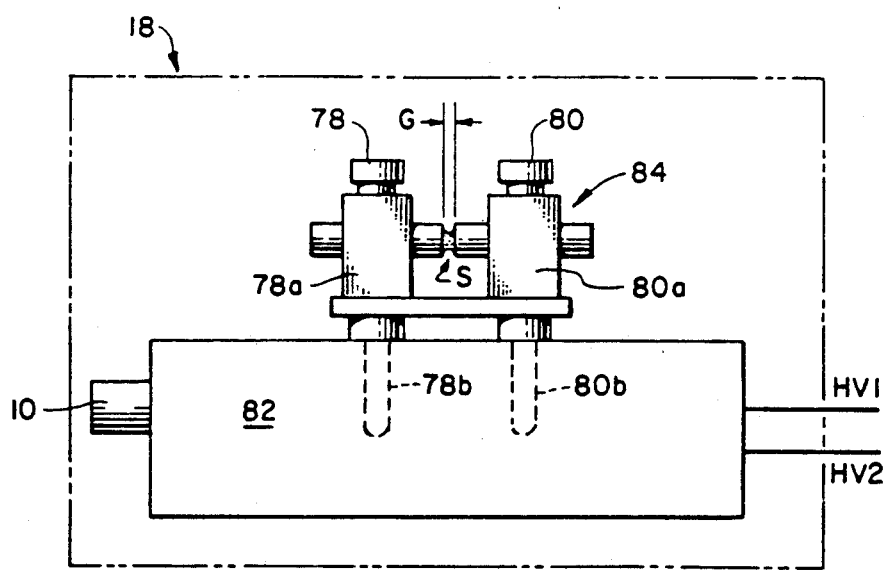
FIG. 4 is a schematic side view of the cell transformation zone of the invention within which the transformation of small batch or sample quantities of suspensions of living cells is conducted by electroporation.

A drawing of the sample transformation zone 18 is shown in FIG. 4. The electrodes 78 and 80 are constructed from high quality stainless steel or other non-reactive metal. They are removable with their supporting structure 78a and 80a, respectively, so that they may be easily cleaned and/or sterilized. The gap "G" between them is adjustable so that the optimum field strength requirements of different cell types may be accommodated by adjusting the gap.

In practice, a drop of cellular suspension S is inserted between the electrodes 78 and 80 using a micropipette device. If ¼" diameter electrodes are used, the practical limits of the sample size are five microliters to fifty microliters. For larger electrodes, the amount of cellular suspension sample may be scaled up according to the electrode surface area. For bacterial cell suspensions, the orientation of the sample of the cell suspension relative to gravity is unimportant. However, for suspensions of cells that are large enough to settle out during the poration process (e.g., plant and animal cells), a vertical orientation of the electrodes is preferred. Such orientation results in cells settling out of suspension on one of the electrodes so that all cells are exposed to the same field strength. After electroporation, the suspension of cells is removed from the electrodes and transformation zone using a micropipette.

The electrodes 78 and 80 are supported in a base holder 82 equipped via banana plugs 78b and 80b, respectively, so that the electrode assembly 84 can be easily plugged into the base holder and unplugged for cleaning. The base holder 82 contains electrical leads HV1 and HV2 for connection to the pulse generator. Further, the base holder 82 includes appropriate electrical instruments (not shown) for monitoring and measuring the electrical pulse characteristics applied to electrodes 78 and 80, as well as the push button switch 10 associated with the control circuit of the electronic circuitry utilized to generate the appropriate transient high intensity electric field required for high efficiency electroporation of cells in accordance with the invention.

Preparation of Cells

In addition to the electrical apparatus for generating and applying the high intensity pulse, the invention includes a method for preparing the cellular suspension in order to maximize the efficiency of transformation. The method involves three steps:

1) Growing the cell culture to an optimal density;
2) Harvesting and washing the cells; and
3) Suspending the cells at an optimal density in a specific poration buffer.

All three steps are critical to the success of the poration procedure. When a bacterial cell culture is grown in a liquid medium, the culture goes through three phases: lag, exponential growth, and then passes into a stationary phase. The susceptibility of the cell wall to the electric pulse varies tremendously over these different phases. In exponential phases, the cells are extremely sensitive to electric pulses; survival can be as low as 0.01%. Of the survivor cells, nearly all may be transformed successfully, but the extremely low cell survival rate makes the overall efficiency of transformation low.

Cells become highly resistant to the pulse as they enter the stationary phase; survival may rise 1000-fold to above 10%. However, each survivor cell may have only a small chance of being transformed. During the transition between the exponential and stationary phases, the survival rate initially rises faster than the efficiency of poration declines. The result is a peak of transformation efficiency at some point during the transition. This peak can be as much as one hundred times the levels at the two extremes. The time at which the maximum efficiency is reached may differ from cell line to cell line, requiring that for the highest efficiency the time of the maximum be determined empirically. The preferred method for monitoring the state of the culture is to measure its light scattering at a wavelength of 650 nanometers, which is proportional to the density of cells in the growth medium. Note that in order for this to work, the same growth medium must be used for all measurements.

The cells are harvested immediately prior to the poration procedure by centrifugation. They must then be washed in very pure water several times to remove any ions left over from the growth medium. The washing may be performed by resuspending the cells in water and then collecting them by centrifugation. Some cell types which are grown in high ionic strength buffers are sensitive to the osmolarity of the solutions used for the washes. In these cell lines, it is preferable to use a 10-20% solution of high purity glycerol, manitol, ficol, or other osmotic agent to maintain the proper osmotic strength, thereby improving survival.

The concentration at which the cells are suspended for the poration procedure, and the solution in which they are suspended, are critical for the success of the poration. The preferred solution for the poration procedure is high purity water. A solution of 10-20% high purity glycerol in water may be used for cell lines that are particularly susceptible to killing by osmotic shock. The DNA should be added to the solution with as little accompanying salts and buffers as possible. If the DNA molecules are the major ionic species in the poration solution, they will then be attracted to the cells during the pulse by mutually induced dipole electrostatic attraction, and the efficiency of transformation will rise.

The volume of solution from which cells can attract DNA molecules is only a few times larger than the cell itself. Therefore, it is useful to concentrate the cells as much as possible so that most of the DNA molecules will be close enough to a cell to participate in a transformation. The preferred method is to collect the cells from the final wash by centrifugation and estimate the volume of the pellet. The cells are then resuspended in double that volume of poration buffer containing DNA. The suspension must be mixed thoroughly to insure that there are no clumps of cells sticking together.

Using a high cell density has the desirable side effect of reducing the field strength necessary to achieve poration. This presumably occurs because the non-porated bacteria are highly conductive and their volume effectively reduces the distance between the electrodes.

Poration Conditions

The field strength at which maximum transformation occurs is determined by the cell type and the concentration at which the cells are suspended in the transformation buffer. The preferred method is to use a concentrated cellular suspension which lowers the optimum field strength to 12,000 volts/cm. If a diluted suspension is used, then the solution itself breaks down and arcs before the optimum field strength can be attained.

Growth of Transformants

Following the pulse, the suspension is allowed to stand at room temperature for ten minutes. After this interval, it may be diluted as needed and appropriate numbers of cells placed on a selective medium solidified with agar to obtain clones of transformed cells.

Recovery of Plasmid DNA

The electroporation apparatus and method may also be used to recover plasmid DNA from transformed cell lines. The procedure is repeated with cultures of transformed cell lines, except that the poration buffer contains no DNA or glycerol. Following the pulse, the suspension is transferred to a tube containing 5–10 volumes of water or buffer, and mixed thoroughly. The cells are removed by centrifugation, leaving the plasmid DNA in the supernatant free of cellular DNA and other contaminants.

Continuous Flow Electroporation

The cell transformation methodology of the invention, including the electroporation of suspensions of cells in admixture with DNA, may be applied to larger volumes of cell suspensions by pumping such suspensions through an electroporation chamber (within a cell transformation zone) shaped so that the high intensity electrical field to which the cells are exposed varies in intensity profile, within preferred time spans, in the same way as does the transient high intensity electrical pulse generated by the circuitry of FIG. 2, although the electroporation chamber itself is electrified with a DC potential. Thus, continuous flow electroporation, as a second preferred embodiment of the invention, may be accomplished by constructing the electroporation chamber, including its electrodes, so that the flow velocity of the cell suspension passing through the chamber varies rapidly with its exposure to the most intense expanse of the electric field within an interval of up to about 100 microseconds. The length of the electroporation chamber, and its venturi configuration and dimensional profile, are based on the suspension flow velocity profile upstream of the chamber's venturi passage, through the venturi throat and passage, and downstream of the venturi passage, together with the electric field intensity created by electrodes which assume the profile of the venturi passage on opposite sides thereof. The flow profile of the cell suspension keeps the cell within the electric field for 2–4 milliseconds (2000–4000 microseconds).

A block diagram of the apparatus for the continuous flow transformation by electroporation of living cells in suspension with DNA is shown in FIG. 5. The cell suspension, prepared as described heretofore, is stored in a reservoir and fed by a high speed pump 92 to the cell transformation zone 94 which includes the continuous flow electroporation chamber 96. In order to generate an electric field strength of 12,000 volts/cm within chamber 96, a potential of 600 volts DC is maintained by power source 97 on the electrodes within the chamber. The velocity of the cell suspension before it enters the electroporation chamber 96 is about 1 meter/second and the maximum velocity of the suspension within the chamber is about 5 meters/second. The porated cell suspension leaving the electroporation chamber 96 within cell transformation zone 94 passes to appropriate cell recovery apparatus 98 wherein the transformed cells in the suspension are separated. Also, plasmid DNA may be recovered from the transformed cell lines.

A schematic side cross-sectional view of the continuous flow electroporation chamber 96 of the invention (within a cell transformation zone 94) is shown in FIG. 6. The chamber 96 is of venturi configuration. The upstream end of the chamber, extending over the distance A, comprises a space which necks down to the venturi throat t. The venturi passage, from its throat t to its outlet end extends over the distance B and is defined on it upper and lower surface by electrode strips 100a and 100b, respectively. The downstream end of chamber 96 extends over the distance C and beyond, as required. The upstream end, venturi passage, and downstream end of the chamber 96 are generally defined by electrical insulation material 102a and 102b. As the cell suspension enters the upstream section of the electroporation chamber 96 its flow velocity is greatly accelerated to maximum flow velocity at venturi throat t. During flow of the cell suspension through the venturi passage over distance b' the flow velocity of the suspension remains nearly at maximum. Over the same distance the close separation spacing of strip electrodes 100a and 100b remains nearly the same whereby the 600 volt DC potential impressed upon such electrodes results in an electric field strength of about 12,000 volts/cm. After the distance b' is reached by the cell suspension flow, the flow velocity of the suspension in the chamber drops off very rapidly over the distance b" because of the great and rapid expansion of the venturi passage and the electric field strength impressed upon the suspension by the downstream ends of the electrodes 100a and 100b falls off greatly as such electrodes diverge. Thus, the flow velocity profile of the cell suspension over the distance B and the DC electric field strength profile over such distance combine to simulate the transient high intensity electric pulse characteristics as created with respect to the electroporation of cells in small batch or sample quantities via the electrode arrangement of FIG. 4 and circuitry of FIG. 2.

It is to be noted that the venturi passageway (within the electroporation chamber 96) does not have a circular cross section. Rather, the chamber has parallel flat side walls 104 which are also formed of appropriate insulating material. In one exemplary construction of a continuous flow electroporation chamber, in accordance with the invention, the throat dimension t of the venturi was 0.5 mm with the width of the electrode strips 100a and 100b being 0.5 cm. With a cell suspension entry flow rate of 1 meter/second and a maximum suspension flow rate of 5 meters/second at the venturi throat, the volume of suspension treated was 125 ml per second or 7 liters per minute.

The continuous flow electroporation apparatus and methodology of the invention may be used either to transform large volumes of living cells in a suspension, or to recover DNA or any other cellular constituent that is released into the suspension by the poration procedure. By placing multiple electroporation chambers in parallel, the procedure may be scaled up to any size.

In the specification and drawing figures there has been set forth preferred embodiments of apparatus and methodology for the transformation of living cells by the introduction of DNA thereto through transient pores created in the cell walls by electroporation. Although specific terms have been employed in describing the invention, they are used in a generic and descriptive sense only and not for purposes of limitation, the scope of the invention being defined in the following claims.

What is claimed is:

1. Apparatus for electroporating living cells in a liquid suspension of said cells and DNA by the introduction of the DNA into said cells through transient pores created in the cell walls, said apparatus comprising:
   a) a pair of spaced electrodes positioned in a cell transformation zone for receiving between the opposing face surfaces of said electrodes a liquid suspension of living cells and DNA, said electrodes comprising a pair of spaced elongated metallic strips;
   b) means for generating across said electrodes and through said liquid suspension of cells a static electric field having a field strength of from about 12,000 to about 15,000 volts per centimeter;
   c) means for passing said liquid suspension of said living cells between said electrodes as a continuous flow; and
   d) means to provide variable flow rates of said liquid suspension of said living cells between said electrodes to effect the initial exposure of said suspension of cells between said electrodes to a maximum level of said field strength for a period of from about 10 to about 100 microseconds and thereafter to effect a reduction of exposure of said suspension of cells between said electrodes to zero field strength over a period of exposure of no more than about 5,000 microseconds.

2. The apparatus for electroporating living cells in a liquid suspension of said cells as claimed in claim 1 wherein the means for passing said liquid suspension of said living cells between said spaced electrodes as a continuous flow comprises a pump and the means to effect variable flow rates of said liquid suspension between said spaced electrodes comprises a passageway with said spaced elongated metallic electrode strips defining a pair of opposing walls thereof and shaped to generate a static electric field of decreasing intensity in the direction of flow of said liquid suspension of said cells such that said cells are exposed to a very rapid rise in field strength to the maximum level of field strength followed by a fall of field strength to zero field strength.

3. The apparatus for electroporating living cells in a liquid suspension of said cells as claimed in claim 1 wherein the means to provide variable flow rates of said liquid suspension or said cells between said spaced electrodes comprises a venturi shaped passageway with said elongated metallic electrode strips defining a pair of opposing walls thereof whereby the configuration and dimensional characteristics of said passageway cause variable flow rates of said liquid suspension of said cells within said passageway which result in the exposure of said cells initially to the maximum field strength intensity between said electrodes within a period of about 10 to about 100 microseconds and thereafter to a reduction in field strength exposure to zero over a period of no more than about 5,000 microseconds.

4. Apparatus for the continuous transformation of the living cells in a liquid suspension of living cells and DNA by the introduction of the DNA into said cells through transient pores created in the cell walls by electroporation said apparatus comprising:
   a) a cell transformation zone having entry means for receiving a flowing liquid suspension of living cells in admixture with DNA, a venturi shaped passageway within said zone wherein said suspension of cells flows initially at a high rate of flow and thereafter at a rapidly decreasing rate of flow, and exit means for removing said suspension of cells from said zone;
   b) pair of spaced elongated metallic electrode strips defining opposing walls of said venturi passageway from the upstream throat end of said passageway to the downstream terminal end of said passageway; and
   c) a source of DC power applied to said electrode strips at a sufficient voltage level to generate therebetween and across said venturi and through said suspension of cells a static electric field having a maximum field strength intensity of from about 12,000 to about 15,000 volts per centimeter at the throat end of said passageway and of decreasing intensity to zero field strength intensity at the terminal end of said passageay whereby the cells of said flowing suspension during their flow through said passageway are exposed to a very rapid rise in electrical field strength to the maximum level of field strength intensity over a period of from about 10 to about 100 microseconds followed by a fall to zero electrical field strength intensity over a period of no more than about 5,000 microseconds thereby promoting and effecting the efficient poration and transformation of said cells with the introduction of DNA thereto.

5. The apparatus for the continuous transformation of the living cells in a liquid suspension of living cells and DNA by the introduction of the DNA into said cells through transient pores created in the cell walls by electroporation as claimed in claim 4 wherein pump means is provided for removing a liquid suspension of living cells in admixture with DNA from a cell suspension reservoir and supplying a continuous flow of said suspension to the entry means of said cells transformation zone.

6. The apparatus for the continuous transformation of the living cells in a liquid suspension of living cells and DNA by the introduction of the DNA into said cells through transient pores created in the cell walls by electroporation as claimed in claim 5 wherein the voltage level applied to said electrode strips by said DC power source to attain a maximum field strength intensity of from aobut 12,000 to about 15,000 volts per centimer between said electrodes is about 600 volts. volts.

* * * * *